US012773500B2

(12) United States Patent
Yamanaka et al.

(10) Patent No.: US 12,773,500 B2
(45) Date of Patent: Oct. 27, 2026

(54) SYRINGE

(71) Applicants: TAISEI KAKO CO., LTD., Osaka (JP); CHUGAI SEIYAKU KABUSHIKI KAISHA, Tokyo (JP)

(72) Inventors: Yuji Yamanaka, Tokyo (JP); Kiichi Egami, Tokyo (JP); Ayano Horikawa, Tokyo (JP); TaijI Horita, Osaka (JP); Yukihiro Ogawa, Osaka (JP); Kensuke Taniguchi, Osaka (JP); Junki Miyagawa, Osaka (JP)

(73) Assignees: TAISEI KAKO CO., LTD., Osaka (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 371 days.

(21) Appl. No.: 18/557,906

(22) PCT Filed: May 2, 2022

(86) PCT No.: PCT/JP2022/019491

§ 371 (c)(1),
(2) Date: Oct. 27, 2023

(87) PCT Pub. No.: WO2022/231012

PCT Pub. Date: Nov. 3, 2022

(65) Prior Publication Data

US 2024/0226443 A1 Jul. 11, 2024

(30) Foreign Application Priority Data

Apr. 30, 2021 (JP) ................................ 2021-077468

(51) Int. Cl.
*A61M 5/315* (2006.01)

(52) U.S. Cl.
CPC ............................... *A61M 5/31513* (2013.01)

(58) Field of Classification Search
CPC .......... A61M 5/31513; A61M 5/31511; A61M 2005/3103; A61M 2005/31598;
(Continued)

(56) References Cited

U.S. PATENT DOCUMENTS 2,688,966 A 9/1954 Huber
3,986,645 A 10/1976 Baldwin et al.
(Continued)

FOREIGN PATENT DOCUMENTS

CN 1874812 A 12/2006
DE 1961166 A1 7/1970
(Continued)

OTHER PUBLICATIONS

Extended Search Report from European Patent Application No. 22795924.4 dated Feb. 27, 2025.
(Continued)

*Primary Examiner* — Serkan Akar
(74) *Attorney, Agent, or Firm* — Ladas & Parry, LLP

(57) ABSTRACT

Provided is a syringe including: a barrel; and a partitioning device, the partitioning device including: a cylindrical housing; and an inner plug, the housing including an engaging part configured to engage with the inner plug in an out-of-communication state, the inner plug including an engaged part configured to engage with the engaging part from a proximal side in the out-of-communication state, and the partitioning device being configured so that, when a pressing force is applied from the proximal side, one of the engaging part and the engaged part rides over an other one thereof and release engagement between the engaging part and the engaged part, thereby allowing the inner plug to have the proximal side space inside the housing and the distal side space inside the housing communicating with each other to
(Continued)

achieve communication between the proximal side space inside the barrel and the distal side space inside the barrel.

2 Claims, 17 Drawing Sheets

(58) Field of Classification Search
CPC .... A61M 5/3145; A61M 5/281; A61M 5/285; A61M 5/3134; A61M 2005/3131; A61M 2205/7545
See application file for complete search history.

(56) References Cited

U.S. PATENT DOCUMENTS

| | | | |
|---|---|---|---|
| 4,233,975 | A | 11/1980 | Yerman |
| 4,464,174 | A | 8/1984 | Ennis |
| 5,613,951 | A | 3/1997 | Meyer et al. |
| 2004/0013861 | A1 | 1/2004 | Miyanaga et al. |
| 2004/0074076 | A1 | 4/2004 | Landau |
| 2015/0018761 | A1 | 1/2015 | Griffiths et al. |

FOREIGN PATENT DOCUMENTS

| | | | |
|---|---|---|---|
| EP | 0112574 | A | 7/1984 |
| JP | S50-100888 | A | 8/1975 |
| JP | 2006-502803 | A | 1/2006 |
| JP | 2007-508898 | A | 4/2007 |
| JP | 4896727 | B | 3/2012 |
| TW | I341214 | B | 5/2011 |
| TW | 201521809 | A | 6/2015 |
| WO | 2015/031677 | A | 3/2015 |

OTHER PUBLICATIONS

International preliminary report on patentability issued in International Application No. PCT/JP2022/019491, issued on Oct. 24, 2023 with English translation provided by WIPO.
Office action from corresponding Taiwanese Patent Application No. 111116593 dated Jul. 2, 2025 with search report.
International Search Report in International Application No. PCT/JP2022/019491, mailed on Jun. 14, 2022, with English translation provided by WIPO.
Written Opinion of the International Searching Authority in International Application No. PCT/JP2022/019491, mailed on Jun. 14, 2022, with English machine translation provided by WIPO.
Office action from corresponding Chinese Patent Application No. 202280030983.6 dated Jul. 25, 2026, with search report.

SYRINGE

CROSS-REFERENCE TO RELATED APPLICATIONS

This application is a 371 national stage application of PCT application No. PCT/JP2022/019491 filed on May 2, 2022, which claims priority to Japanese Patent Application No. 2021-077468, the disclosures of which are incorporated herein by reference in their entireties.

FIELD

The present invention relates to a syringe including an inner plug for partitioning a space inside a barrel, the inner plug being opened when in use.

BACKGROUND

Conventionally known is a syringe configured to mix a plurality of contents together when in use for injection (Patent Literature 1). As shown in FIG. 15, the syringe includes a chamber 105, a needle 104, and a plunger 103. A space inside the chamber 105 is partitioned into a wet portion S101 and a dry portion S102 by a sealing mechanism 107. The plunger 103 is disposed at a rearward end of the chamber 105 so as to be slidable forward. The plunger 103 seals the wet portion S101. The sealing mechanism 107 engages with an inner circumferential surface of the chamber 105 to prevent a content in the wet portion S101 (e.g., injection solution) from passing into the dry portion S102 before use.

As shown in FIG. 16, the sealing mechanism 107 includes an outer sealing member 108 having a substantially circular cylindrical shape, and a movable sealing plug 109 sealingly engaging with an inner circumferential surface of the outer sealing member 108. The inner circumferential surface of the outer sealing member 108 has a plurality of grooves 180 each extending forward in a longitudinal direction. These grooves 180 form a flow channel 181.

In this syringe, the plunger 103 is slid forward for pressurization to thereby move the sealing plug 109 forward from a first sealing position (FIG. 16) at which the sealing plug 109 sealingly engages with the inner circumferential surface of the outer sealing member 108 to a second bypass position (FIG. 17). This allows the injection solution inside the wet portion S101 to flow through the flow channel 181 into the dry portion S102.

CITATION LIST

Patent Literature

Patent Literature 1: JP 4896727 B

SUMMARY

Technical Problem

However, when pressurization is made by the plunger 103 to move forward the sealing plug 109, there are some cases where the sealing plug 109 becomes inclined relative to a cylindrical axis of the outer sealing member 108. When the sealing plug 109 is inclined as above, the flow channel 181 may partially open before the sealing plug 109 reaches the second bypass position. In this case, there is a likelihood of failing to secure a sufficient width of the flow channel, consequently increasing discharging resistance of the injection solution.

Such a problem is not limited to the case where a plurality of contents are mixed together when in use for injection. The problem can occur in any case where a space within a barrel such as a chamber is partitioned before use and the partitioned space is made to communicate with each other when in use.

It is an object of the present invention to provide a syringe in which a partitioning device for partitioning a space inside a barrel can be opened when in use for smooth discharge of a medical liquid.

Solution to Problem

A syringe of the present invention is a syringe for injecting a medicine, the syringe including: a barrel having a cylindrical shape with a distal end part and a proximal end part and having an outlet opening in the distal end part for discharging the medicine contained inside the barrel to an outside; and a partitioning device for partitioning a space inside the barrel into a proximal side space and a distal side space, the partitioning device including: a cylindrical housing disposed to come into liquid-tight contact with an inner surface of the barrel; and an inner plug disposed to allow a proximal side space inside the housing and a distal side space inside the housing to be opened and closed so that the proximal side space inside the barrel and the distal side space inside the barrel are brought into or out of communication with each other through an inside of the housing, the housing including an engaging part configured to engage with the inner plug when the proximal side space inside the housing and the distal side space inside the housing are not in communication with each other, the inner plug including an engaged part configured to engage with the engaging part from a proximal side when the proximal side space inside the housing and the distal side space inside the housing are not in communication with each other, and the partitioning device being configured so that, when a pressing force is applied from the proximal side by a piston inserted from the proximal side into the barrel, one of the engaging part and the engaged part is displaced relative to an other one of the engaging part and the engaged part to cross over or ride over the other one and release engagement between the engaging part and the engaged part, thereby allowing the inner plug to have the proximal side space inside the housing and the distal side space inside the housing communicating with each other to achieve communication between the proximal side space inside the barrel and the distal side space inside the barrel.

The syringe can be configured such that the engaging part includes a proximal side engaging part and a distal side engaging part disposed respectively on a proximal side and a distal side of the engaged part, or the engaged part includes a proximal side engaged part and a distal side engaged part disposed respectively on a proximal side and a distal side of the engaging part.

The syringe can be configured to further include a filter disposed on a distal side end surface of the housing inside the barrel.

The syringe can be configured such that the partitioning device is disposed in the distal end part of the barrel.

DESCRIPTION OF EMBODIMENTS

A description will be hereinafter given on a prefilled syringe provided with a syringe according to an embodiment of the present invention, with reference to FIG. 1 to FIG. 6.

Figure 1:
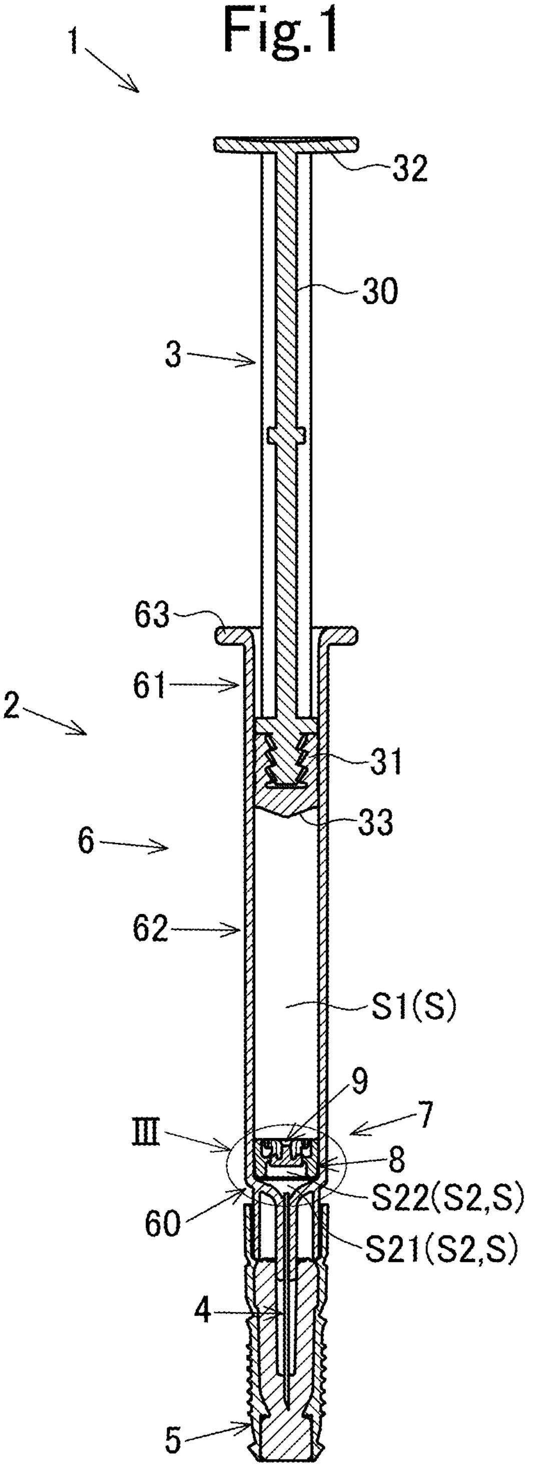
FIG. 1 is a cross-sectional view of a prefilled syringe including a syringe according to this embodiment, for explaining a closed state of an inner plug within the prefilled syringe.
Figure 2:
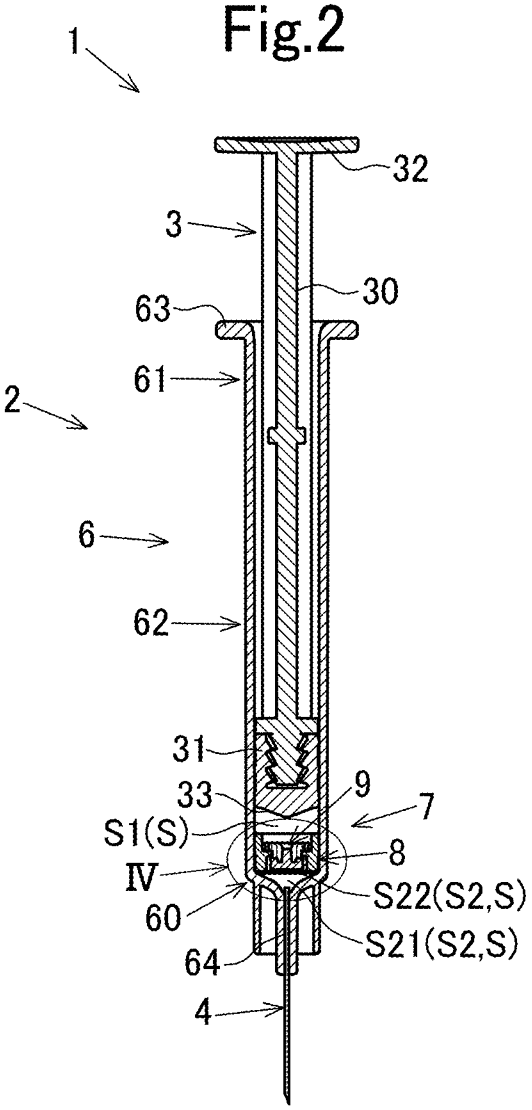
FIG. 2 is a cross-sectional view of the prefilled syringe for explaining an open state of the inner plug within the prefilled syringe.

As shown in FIG. 1 and FIG. 2, a prefilled syringe 1 includes a syringe 2 for injecting a medicine. The prefilled syringe 1 further includes a piston 3 inserted into the syringe 2. Furthermore, the prefilled syringe 1 includes an injection needle 4 connected to the syringe 2. The prefilled syringe 1 includes a cap 5 that covers the injection needle 4. The medicine is a liquid medicine, and is, for example, a protein preparation.

The syringe 2 includes a barrel 6 having a cylindrical shape with a distal end part 60 and a proximal end part 61, and a partitioning device 7 for partitioning a space S inside the barrel 6 into a proximal side space S1 and a distal side space S2. Further, the syringe 2 has a substantially cylindrical shape.

Hereinafter, in the prefilled syringe 1 and the syringe 2, a side on which the distal end part 60 is disposed (lower side in FIG. 1 to FIG. 4) is simply referred to as "distal side", and a side on which the proximal end part 61 is disposed (upper side in FIG. 1 to FIG. 4) is referred to as "proximal side". Also, an axial direction of the syringe 2 is simply referred to as "axial direction".

The barrel 6 is a member for containing a medicine thereinside. In the barrel 6, the distal end part 60 is provided with a discharging hole for discharging to the outside the medicine contained inside the barrel 6. In this embodiment, the barrel 6 includes, in addition to the distal end part 60 and the proximal end part 61, a cylindrical part 62 connecting the distal end part 60 and the proximal end part 61 to each other. Further, the barrel 6 includes a flange part 63 extending outward from the entire outer circumference of the cylindrical part 62 (i.e., extending radially outward of the cylindrical part 62) at an other end in the axial direction of the cylindrical part 62.

The barrel 6 is made of, for example, a material that is transparent and that can withstand the internal pressure applied thereto at the time of injecting the medicine. Specifically, the material of the barrel 6 is a resin having a cyclic olefin such as norbornene in a repeating unit. More specifically, the material of the barrel 6 is a transparent resin such as a COP (cycloolefin polymer) which is a homopolymer of a cyclic olefin, or a COC (cycloolefin copolymer) which is a copolymer of a cyclic olefin and ethylene or the like. The material of the barrel 6 can be PP (polypropylene) or glass.

Silicon oil can be applied to an inner surface of the barrel 6 (e.g., an inner surface of the cylindrical part 62) to reduce sliding resistance of the piston 3 to an inner circumferential surface of the barrel 6.

Figure 3:
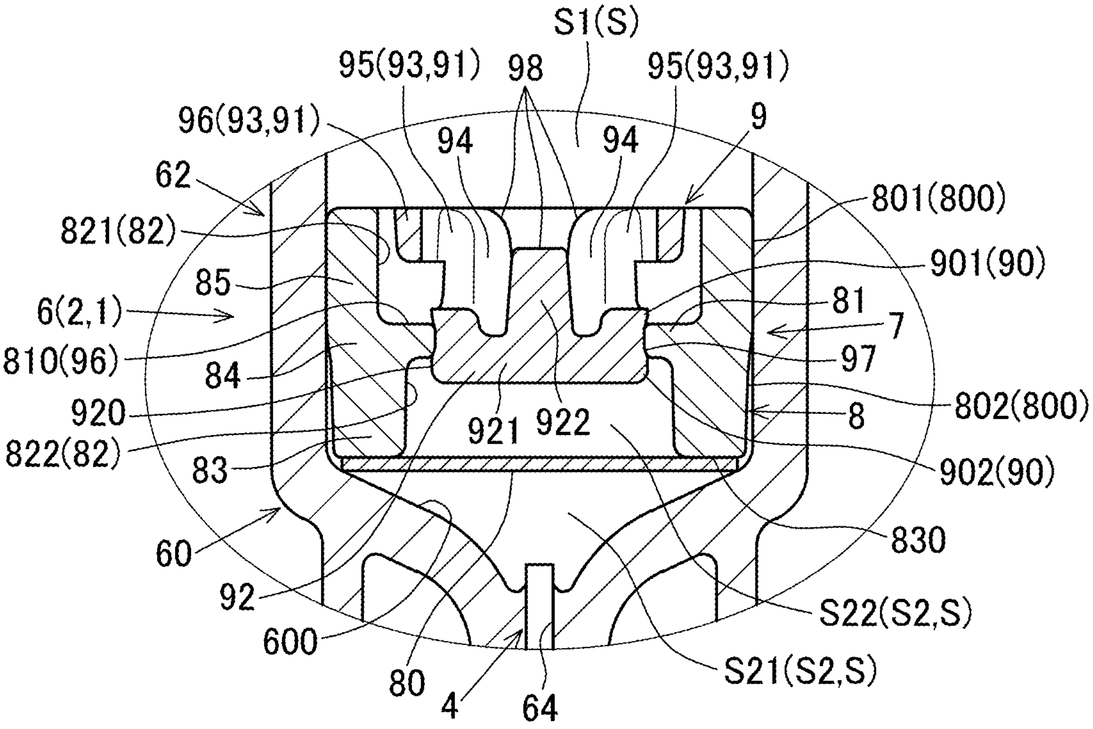
FIG. 3 is an enlarged cross-sectional view of the area indicated by III in FIG. 1.
Figure 4:
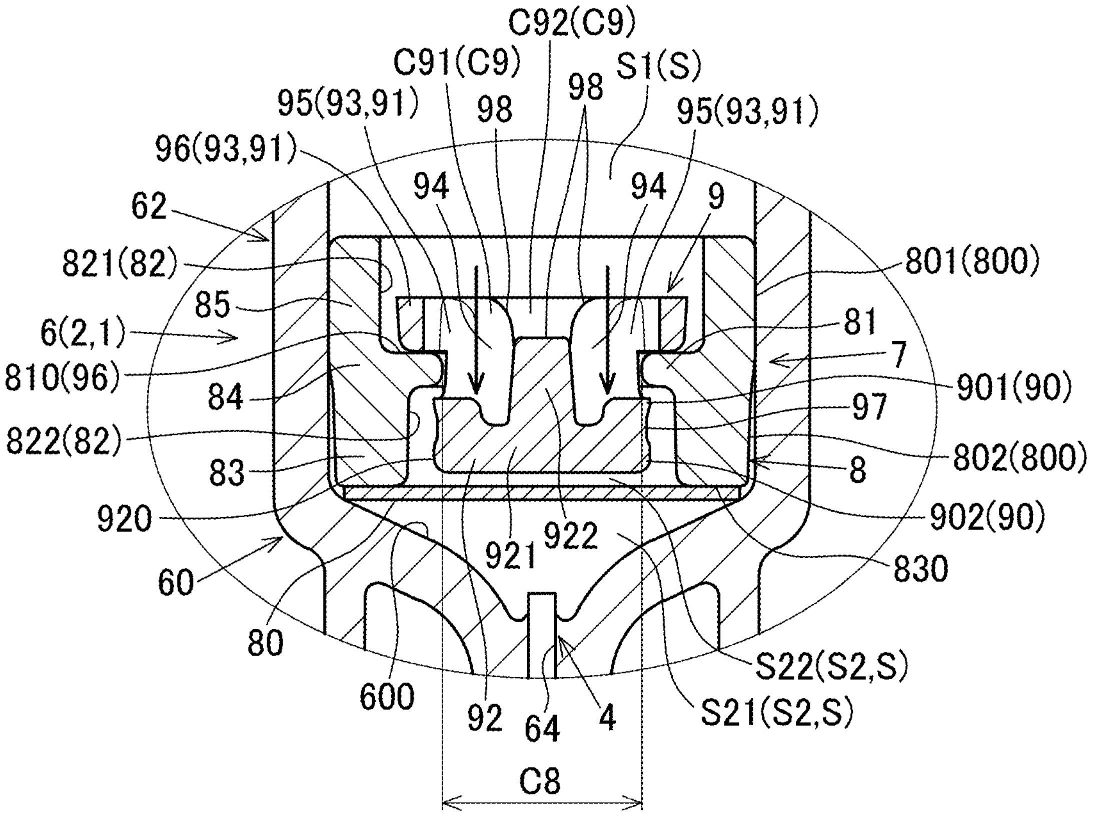
FIG. 4 is an enlarged cross-sectional view of the area indicated by IV in FIG. 2.

The distal end part 60 of the barrel 6 is located at one end in the axial direction of the cylindrical part 62 (specifically, an end part on the distal side). As shown in FIG. 3 and FIG. 4, the distal end part 60 is provided with an outlet opening 64 for discharging to the outside the medicine contained inside the barrel 6. In the barrel 6 of this embodiment, the outlet opening 64 is a hole through which the injection needle 4 is inserted.

When the needle being inserted through the outlet opening 64 is, for example, a 27-gauge needle, the inner diameter of the outlet opening 64 is 0.27 mm and the area of the outlet opening 64 as viewed from the axial direction (i.e., the cross-sectional area of the outlet opening 64 in a direction orthogonal to the axial center) is 0.057 $mm^2$. When the needle being inserted through the outlet opening 64 is a 29-gauge needle, the inner diameter of the outlet opening 64 is 0.21 mm and the area of the outlet opening 64 as viewed from the axial direction is 0.035 $mm^2$. The cross-sectional area in the direction orthogonal to the axial center of the outlet opening 64 is substantially constant in the axial direction. The distal end part 60 has a proximal end surface 600 formed to close an edge portion on the distal side of the cylindrical part 62 except the outlet opening 64. The proximal end surface 600 extends, for example, in an inclined manner to be positioned closer to the distal side as it advances radially inward.

The area of the cylindrical part 62 as viewed from the axial direction (i.e., the cross-sectional area of the cylindrical part 62 in the direction orthogonal to the axial center) is for example substantially constant in the axial direction, and specifically 12.56 $mm^2$ or more and 314 $mm^2$ or less. The inner diameter of the cylindrical portion 62 is for example substantially constant in the axial direction, and specifically 4 mm or more and 20 mm or less.

Such a barrel 6 has the partitioning device 7 housed thereinside, and the partitioning device 7 partitions the space S inside the barrel 6 into the proximal side space S1 on the proximal side in the axial direction and the distal side pace S2 on the distal side in the axial direction. In the barrel 6 of this embodiment, a liquid medicine is contained in the proximal side space S1, which is a space on the proximal side of the partitioning device 7, as shown in FIGS. 1 to 4. The distal side space S2, which is a space on the distal side of the partitioning device 7, is empty with no medicine contained therein. Specifically, the distal side space S2 includes a first distal side space S21 located on the distal side of a filter 80 and having no medicine contained therein, and a second distal side space S22 located on the proximal side of the filter 80 and having no medicine contained therein.

Either the first distal side space S21 or the second distal side space S22 can have a solid medicine contained therein. Each of the proximal side space S1 and the distal side space S2 can have a liquid medicine contained therein.

The partitioning device 7 includes a cylindrical housing 8, and the inner plug 9 capable of being opened and closed relative to the inside of the housing 8. In this embodiment, the partitioning device 7 includes one housing 8 and one inner plug 9. The partitioning device 7 is disposed in the distal end part 60 of the barrel 6 (see FIG. 3 and FIG. 4). Further, the partitioning device 7 includes the filter 80 attached to the housing 8 inside the barrel 6. The partitioning device 7 includes a single filter 80, but can include a plurality of filters 80 layered on each other.

The partitioning device 7 can include no filter 80. In this case, the partitioning device 7 includes, for example, the cylindrical housing 8, and the inner plug 9 capable of being opened and closed relative to the inside of the housing 8.

The housing 8 is a member disposed to come into liquid-tight contact with the inner surface of the barrel 6 (e.g., inner surface of the cylindrical part 62). The housing 8 is housed in the barrel 6 in a state of being in pressure contact with the barrel 6. Specifically, at least a part of an outer circumferential surface 800 of the housing 8 is in close contact with the inner surface of the barrel 6.

In this embodiment, the outer circumferential surface 800 of the housing 8 includes a proximal outer circumferential surface part 801 disposed on the proximal side, and a distal outer circumferential surface part 802 disposed on the distal side, and the distal outer circumferential surface part 802 has a smaller diameter than that of the proximal outer circumferential surface part 801. The proximal outer circumferential surface part 801 comes into liquid-tight contact with the inner circumferential surface of the barrel 6. The distal outer circumferential surface part 802 is opposed to the inner circumferential surface of the barrel 6 with a clearance therebetween.

The housing 8 is made of a flexible material. The housing 8 of this embodiment is more flexible than the barrel 6. Specifically, the material of the housing 8 is, for example, a resin, a rubber, an elastomer, or the like, which is softer than the material of the barrel 6. The flexibility of the barrel 6 and the housing 8 can be confirmed by, for example, measuring their durometer hardnesses. The housing 8 made of such a material can ensure its flexibility relative to the barrel 6 to prevent cracks of the barrel 6.

The housing 8 has a circular cylindrical shape. In this embodiment, the housing 8 is disposed on the proximal side of the filter 80. In other words, the housing 8 is formed only of a proximal side portion disposed on the proximal side of the filter 80.

The housing 8 is formed only of the proximal side portion in this embodiment, but can include a distal side portion that is disposed on the distal side of the filter 80 and is formed integrally with or separately from the proximal side portion.

The housing 8 includes an engaging part 81. Specifically, the housing 8 has one engaging part 81. The engaging part 81 is a member configured to engage with the inner plug 9 when the inner plug 9 is in the closed state (i.e., when a proximal side space inside the housing 8 and a distal side space inside the housing 8 are not in communication with each other; see FIG. 3).

The engaging part 81 projects radially inward from an inner circumferential surface 82 of the housing 8, and is continuously formed across the entire circumference in the circumferential direction or is intermittently formed at intervals across the entire circumference. In this embodiment, the engaging part 81 is a rib projecting from the inner circumferential surface 82 of the housing 8 toward the cylindrical axis (i.e., radially inward). Specifically, the engaging part 81 is a rib continuous in the circumferential direction. Further, the engaging part 81 is disposed in a central part in the axial direction of the inner circumferential surface 82. The engaging part 81 has a proximal side end surface being a radially extending flat surface.

In this embodiment, the inner circumferential surface 82 of the housing 8 includes a proximal inner circumferential surface part 821 disposed on the proximal side, and a distal inner circumferential surface part 822 disposed on the distal side, and the proximal inner circumferential surface part 821 has a larger diameter than that of the distal inner circumferential surface part 822.

The housing 8 configured as above includes the small-diameter inner circumferential surface (specifically, the distal inner circumferential surface part 822) on the distal side, the large-diameter inner circumferential surface (specifically, the proximal inner circumferential surface part 821) on the proximal side, and the engaging part 81 between the small-diameter inner circumferential surface and the large-diameter inner circumferential surface.

The housing 8 includes a stepped surface 810 extending radially inward from the inner circumferential surface 82 and opposed to the proximal side. In this housing 8, the proximal side end surface of the engaging part 81 serves as the stepped surface 810, but the stepped surface 810 can be a surface of a portion different from the engaging part 81. Further, the stepped surface 810 can be positioned on either the distal side or the proximal side of the engaging part 81.

In this embodiment, the housing 8 includes an attachment portion 83 to which the filter 80 is attached, a body portion 84 at which the engaging part 81 is located, and an extending portion 85 extending from the body portion 84. In this housing 8, the attachment portion 83, the body portion 84, and the extending portion 85 are arranged in this order from the distal side to the proximal side. Further, in this housing 8, the attachment portion 83, the body portion 84, and the extending portion 85 each have a circular cylindrical shape. The thickness of the housing 8 (i.e., the distance between the inner circumferential surface and the outer circumferential surface of the housing 8 in a radial direction perpendicular to the axial direction) is not uniform. Specifically, the attachment portion 83 is thicker than the extending portion 85.

The outer circumferential surface of the attachment portion 83 is located slightly away from the inner circumferential surface of the barrel 6 (specifically, the inner circumferential surface of the cylindrical part 62 of the barrel 6). Further, the attachment portion 83 has a tapered shape having a smaller outer diameter as it advances to the distal side. The inner circumferential surface of the attachment portion 83 has a tapered shape having a larger inner diameter as it advances to the distal side.

The body portion 84 is a portion connecting the attachment portion 83 and the extending portion 85 to each other. The outer circumferential surface of the body portion 84 is located slightly away from the inner circumferential surface of the barrel 6 (specifically, the inner circumferential surface of the cylindrical part 62 of the barrel 6). Further, the body portion 84 has a tapered shape having a smaller outer diameter as it advances to the distal side. The inner circumferential surface of the body portion 84 is formed of a projecting end surface of the engaging part 81. The inner circumferential surface of the body portion 84 is located on the radially innermost side of the inner circumferential surface of the housing 8.

The outer circumferential surface of the extending portion 85 is in surface contact with the inner circumferential surface of the barrel 6 (specifically, the inner circumferential surface of the cylindrical part 62 of the barrel 6). The configuration that the outer circumferential surface of the extending portion 85 is in close contact with the inner circumferential surface of the barrel 6 can prevent the medicine from leaking out to the distal side through between the outer circumferential surface of the housing 8 and the inner circumferential surface of the barrel 6. The inner circumferential surface of the extending portion 85 is located radially outside the inner circumferential surface of the attachment portion 83. That is, the extending portion 85 has a larger inner diameter than the inner diameter of the attachment portion 83.

In the housing 8 configured as above, a liquid flow channel C8 is formed radially inside the engaging part 81 that serves as a flow channel for the medical liquid from the proximal side space S1 to the distal side space S2 (see FIG. 4). That is, the liquid flow channel C8 is formed inside the inner circumferential surface of the body portion 84.

The inner plug 9 is a member disposed to be capable of opening and closing the proximal side space inside the housing 8 and the distal side space inside the housing 8 so as to bring the proximal side space S1 (proximal side pace S1 inside the barrel 6) and the distal side space S2 (distal side space S2 inside the barrel 6) into or out of communication with each other through the inside of the housing 8. The inner plug 9 is a plug disposed inside the housing 8 in this embodiment, but can be a lid that covers the housing 8 from the distal side.

The inner plug 9 includes an engaged part 90 configured to engage with the engaging part 81 from the proximal side when the inner plug 9 is in the closed state (i.e., when the proximal side space inside the housing 8 and the distal side space inside the housing 8 are not in communication with each other) (see FIG. 3). The engaged part 90 is disposed on the distal side and the proximal side of the engaging part 81. Specifically, the engaged part 90 includes a proximal side engaged part 901 located on the proximal side, and a distal side engaged part 902 located on the distal side. That is, the inner plug 9 includes a plurality of (e.g., two) engaged parts 90.

The inner plug 9 includes a restricting device 91 configured to restrict the inner plug 9 from moving to the distal side when the engagement between the engaging part 81 and the engaged parts 90 is released to bring the proximal side space S1 and the distal side space S2 into communication with each other. The inner plug 9 including the restricting device 91 is prevented from blocking a flow channel such as the outlet opening 64 when the proximal side space S1 and the distal side space S2 are in communication with each other.

In this embodiment, the inner plug 9 located at a position away on the proximal side from the filter 80 is restricted by the restricting device 91 from moving to the distal side. This configuration can prevent the inner plug 9 from clogging the filter 80.

The inner plug 9 includes a lid portion 92 having the engaged parts 90 on its outer circumferential surface and configured to be capable of opening and closing the liquid flow channel C8 of the housing 8. Further, the inner plug 9 has a step engaging part 93 disposed on the proximal side of the lid portion 92 and projecting more radially outward than the lid portion 92, and a plug channel C9 located radially inside the step engaging part 93 and formed between the lid portion 92 and the step engaging part 93 (see FIG. 4). With this configuration, when the inner plug 9 is restricted in the open state, the medical liquid contained in the proximal side space S1 flows within the liquid flow channel C8 formed radially inside the engaging part 81 from the proximal side to the distal side (in the arrowed direction in FIG. 4) through the plug channel C9 formed radially inside the step engaging part 93, and further flows through between the lid portion 92 and the engaging part 81 smoothly into the distal side space S2. Further, the configuration that an outer circumferential part 920 of the lid proportion 92 is not in contact with the inner circumferential surface part 822 of the housing 8 over the entire circumference enables the medical liquid to flow uniformly across the entire circumference.

In this embodiment, the inner plug 9 includes, as the restricting device, the stepped surface 810 and the step engaging part 93 projecting radially outward and capable of engaging with the stepped surface 810 from the proximal side. The restricting device 91 including the stepped surface 810 and the step engaging part 93 allows the step engaging part 93 to engage with the stepped surface 810 from the proximal side, thereby being capable of securely restricting the movement of the inner plug 9.

The step engaging part 93 is, for example, provided continuously or intermittently across the entire circumference in the circumferential direction. In this embodiment, the step engaging part 93 is provided continuously. In such a configuration, the step engaging part 93 provided continuously or intermittently across the entire circumference in the circumferential direction comes into engagement with the stepped surface 810 from the proximal side to restrict the inner plug 9 from moving to the distal side, at the time when the engagement between the engaging part 81 and the engaged parts 90 is released to allow the inner plug 9 to move to the distal side and bring the proximal side space S1 and the distal side space S2 into full communication with each other. Since both the step engaging part 93 and the stepped surface 810 are formed across the entire circumference radially outside the lid portion 92, the inner plug 9 keeps its stable posture and is restricted from moving.

Figure 5:
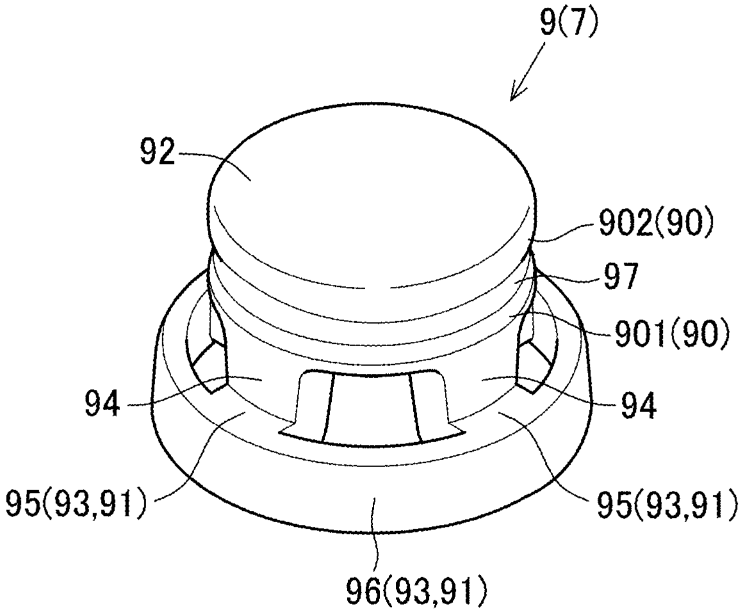
FIG. 5 is a perspective view of the inner plug in the syringe.
Figure 6:
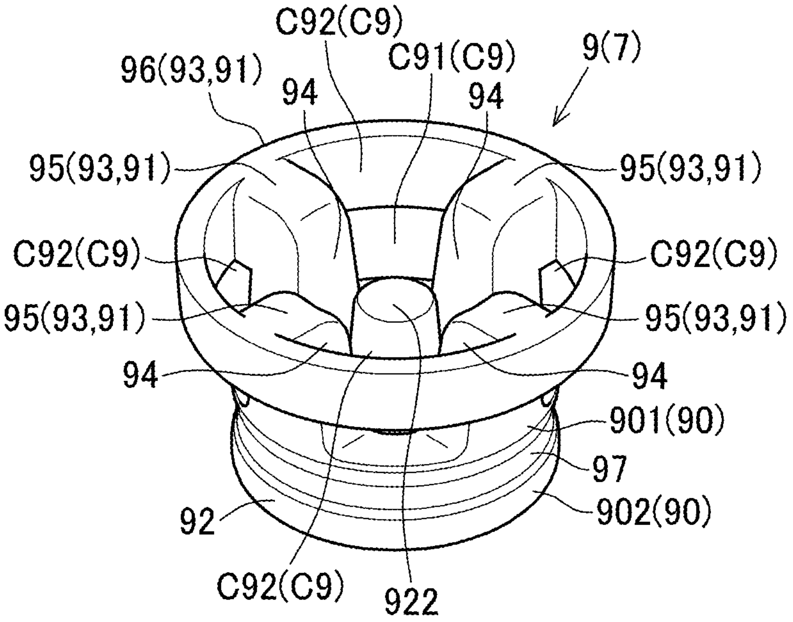
FIG. 6 is a perspective view of the inner plug.
Figure 7:
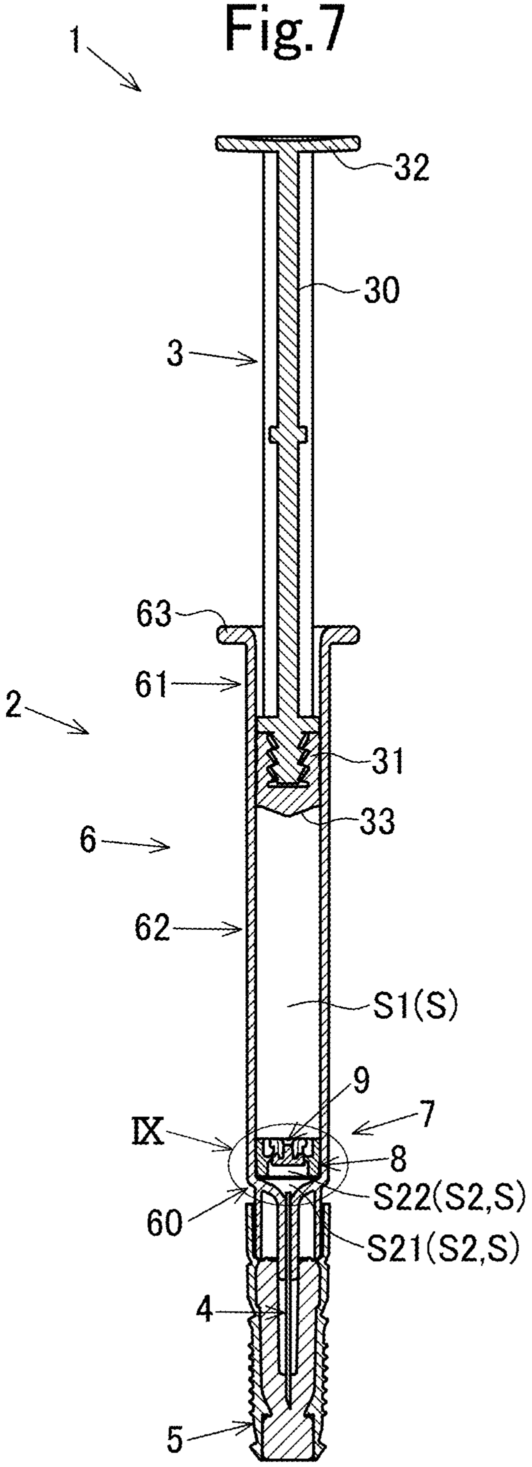
FIG. 7 is a cross-sectional view of a prefilled syringe according to a modified example for explaining a closed state of an inner plug within the prefilled syringe.
Figure 8:
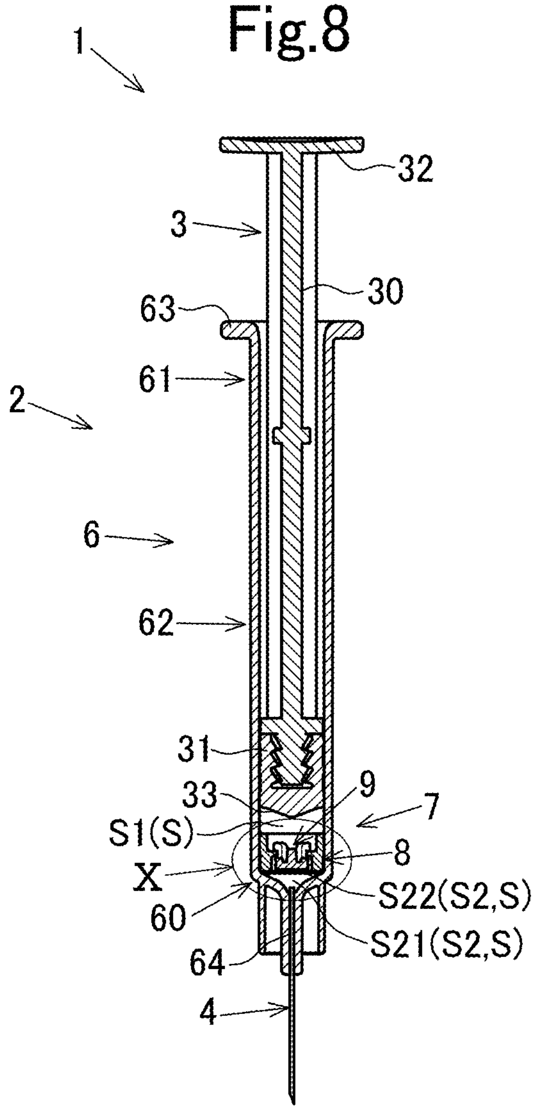
FIG. 8 is a cross-sectional view of the prefilled syringe for explaining an open state of the inner plug within the prefilled syringe.
Figure 9:
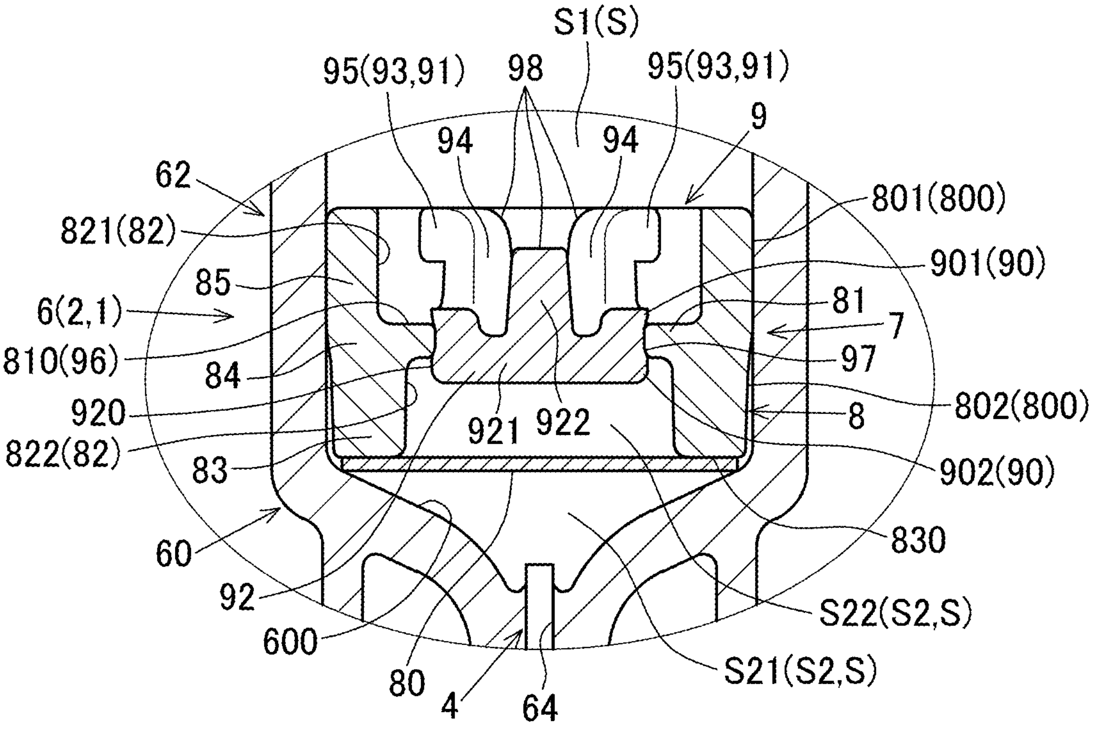
FIG. 9 is an enlarged cross-sectional view of the area indicated by IX in FIG. 7.
Figure 10:
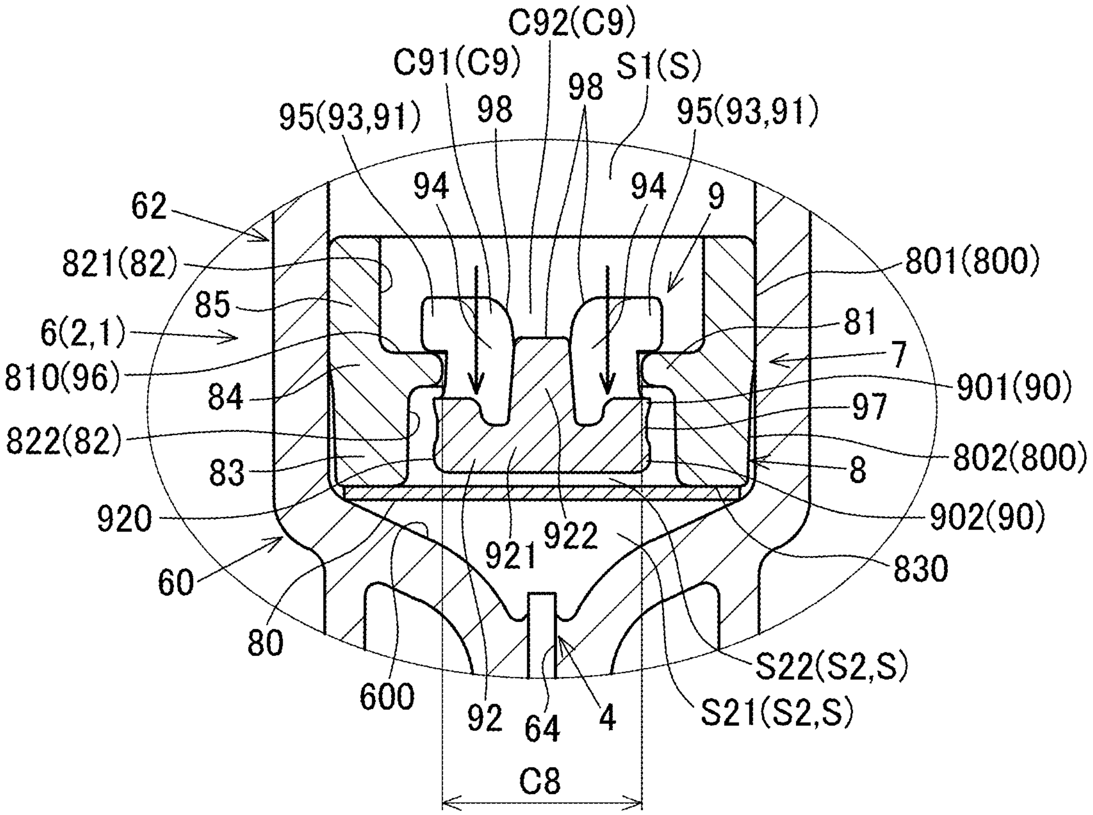
FIG. 10 is an enlarged cross-sectional view of the area indicated by X in FIG. 8.
Figure 11:
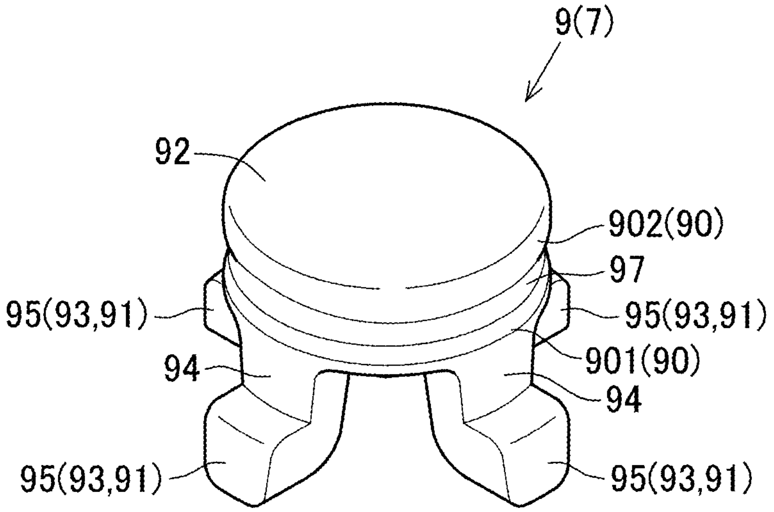
FIG. 11 is a perspective view of the inner plug in the syringe.
Figure 12:
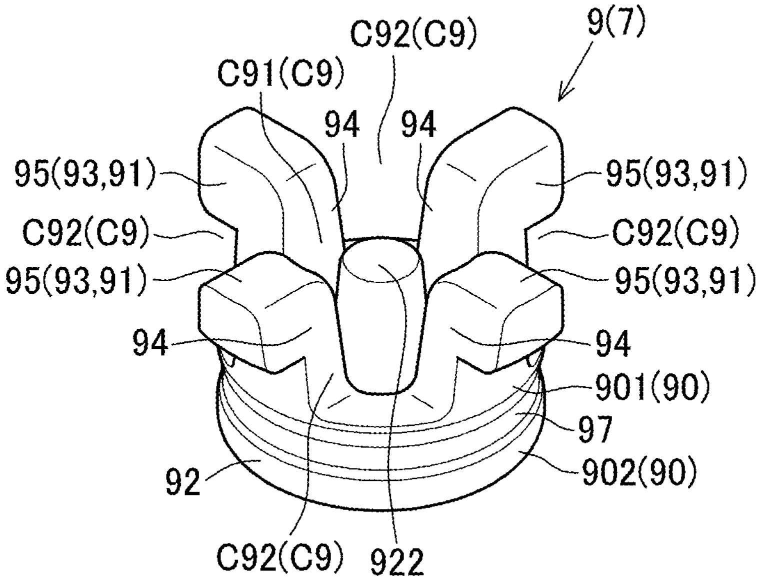
FIG. 12 is a perspective view of the inner plug.

In addition to the lid portion 92, the inner plug 9 includes a leg portion 94 extending from the lid portion 92. In this embodiment, as shown in FIG. 5 and FIG. 6, the inner plug 9 includes a plurality of the leg portions 94 (specifically four leg portions 94). The inner plug 9 further includes a plurality of projecting portions 95 (specifically, four projecting portions 95) extending from the respective leg portions 94 toward the housing 8 (i.e., radially outward). Furthermore, the inner plug 9 includes an annular portion 96 connecting the plurality of projecting portions 95 with each other.

The inner plug 9 includes the projecting portions 95 as the step engaging part 93, and more specifically, the inner plug 9 includes, as the step engaging part 93, the annular portion 96 in addition to the projecting portion 95.

The lid portion 92 is a portion fitted to the inside of the housing 8 (see FIG. 3 and FIG. 4). The lid portion 92 is a portion having the engaged parts 90 on its outer circumferential surface and configured to be capable of opening and closing relative to the inside of the housing 8. Further, the lid portion 92 is a portion as a partition between the proximal side space S1 and the distal side space S2. For example, the lid portion 92 has a substantially disk shape. The outer circumferential part 920 of the lid portion 92 is provided with the engaged parts 90. An inner circumferential part 921 of the lid portion 92 (a portion of the lid portion 92 located radially inside the outer circumferential part 920) has a lid leg 922 extending from the disk portion to the proximal side. In this embodiment, a proximal side end surface of the lid leg 922 is located on the distal side of proximal side end surfaces the leg portions 94. The proximal side end surface of the lid leg 922 is located on the distal side of proximal side end surfaces of the projecting portions 95. Further, the proximal side end surface of the lid leg 922 is located on the distal side of a proximal side end surface of the annular portion 96.

The lid leg 922 is disposed to project from a radial center of the lid portion 92 to the proximal side. The lid leg 922 has a smaller outer diameter than the outer diameter of the lid portion 92. The lid leg 922 is disposed at a radial center of an area enclosed by the plurality of leg portions 94 (plurality of projecting portions) arranged in the circumferential direction. The lid leg 922 is disposed at a radial center of an area enclosed by the annular portion 96.

The engaged parts 90 are, for example, projections projecting toward the housing 8. Specifically, the engaged parts 90 are ribs projecting toward the housing 8. In this embodiment, each of the engaged parts 90 is a rib provided continuously in the circumferential direction, and can be a plurality of ribs provided at intervals across the entire circumference in the circumferential direction.

The proximal side engaged part 901 is disposed at in an end part on the proximal side of the lid portion 92. The distal side engaged part 902 is disposed in an end part on the distal side of the lid portion 92.

The proximal side engaged part 901 and the distal side engaged part 902 are disposed away in the axial direction from each other. A lid recess 97 is formed between the proximal side engaged part 901 and the distal side engaged part 902. The engaging part 81 of the housing 8 is fitted to the lid recess 97 from the radially outside. In this fitted state, the proximal side engaged part 901 engages with the engaging part 81 from the proximal side to restrict the inner plug 9 from moving to the distal side relative to the housing 8. Further, in the fitted state, the distal side engaged part 902 engages with the engaging part 81 from the distal side to restrict the inner plug 9 from moving to the proximal side relative to the housing 8.

Each of the leg portions 94 is a portion extending to the proximal side from an end on the proximal side of the outer circumferential part 920 of the lid portion 92. The plurality of leg portions 94 (specifically, four leg portions 94) are arranged at equal intervals from each other in the circumferential direction.

The plug channel C9 is formed radially inside the leg portions 94. The plug channel C9 includes an axial channel C91 formed in the axial direction radially inside the leg portions 94, and a communicating channel C92 communicating the axial channel C91 with a space radially outside the leg portions 94 (see FIG. 4). The axial channel C91 is disposed radially inside the projecting portions 95, and is formed along the axial direction between the projecting portions 95 and the lid portion 92. The communicating channel C92 is formed between each adjacent two of the plurality of leg portions 94 and opened radially outward to communicate with the axial channel C91 at a position radially outside the axial channel C91.

Each of the projecting portions 95 is a portion extending toward the housing 8 from an end on the proximal side of each corresponding one of the leg portions 94. The plurality of projecting portions 95 (specifically, four projecting portions 95) are disposed at equal intervals from each other in the circumferential direction.

The annular portion 96 is a portion that connects ends on the housing 8 side of the respective projecting portions 95 (i.e., radially outside ends) with each other. The annular portion 96 has, for example, a circular annular shape. The annular portion 96 can have an annular shape other than the circular annular shape, such as an angular cylindrical shape.

In the inner plug 9 configured as above, in the state where the inner plug 9 is opened, the step engaging part 93 of the inner plug 9 (specifically, the projecting portions 95; in this embodiment, the projecting portions 95 and the annular portion 96) engages with the stepped surface 810 of the housing 8 (i.e., proximal side end surface of the engaging part 81) to thereby restrict the inner plug 9 from further moving to the distal side (i.e., restrict the inner plug 9 from falling off the engaging part 81).

The piston 3 to be inserted into the barrel 6 from the proximal side can come into abutting contact with the inner plug 9. That is, the inner plug 9 includes an abutting surface 98 with which the piston 3 to be inserted can come into abutting contact.

The abutting surface 98 is an end surface on the proximal side of the inner plug 9. Specifically, the abutting surface 98 is formed of an end surface on the proximal side of the lid portion 92. More specifically, the abutting surface 98 is formed of the proximal side end surface of the lid leg 922 and the proximal side end surfaces of the leg portions 94.

The inner plug 9 is formed of a flexible material. The inner plug 9 of this embodiment is more flexible than the barrel 6. Specifically, the material of the inner plug 9 is, for example, a resin, a rubber, an elastomer, or the like, which is softer than the barrel 6. The flexibility of the inner plug 9 can be confirmed by, for example, measuring its durometer hardness. The material of the inner plug 9 is, for example the same as the material of the housing 8, but can be different from the material of the housing 8.

The filter 80 is a filter for filtering the medicine. The filter 80 is disposed on the distal side end surface of the housing 8 (in this embodiment, a distal end surface 830 of the attachment portion 83 of the housing 8), and is disposed on the proximal side of the outlet opening 64 inside the barrel 6.

In this embodiment, the filter 80 is attached to the distal side end surface of the housing 8, specifically, welded to the distal end surface 830. This welding is ultrasonic welding, but a different welding method such as heat welding can be used. The filter 80 can adhere to the distal end surface 830.

The filter 80 can be made of, for example, a membrane, a mesh, a sintered body, or a foam body. The material of the filter 80 is a resin, a ceramic, a metal, paper, or the like. In this embodiment, the filter 80 is, for example, a membrane filter. The filter 80 can be a prefilter.

In the syringe 2 configured as above, when the partitioning device 7 is applied with pressing force from the proximal side by the piston 3 inserted into the barrel 6 from the proximal side, one of the engaging part 81 and the engaged part 90 is displaced relative to the other one to thereby cross over or ride over the other one and release the engagement between the engaging part 81 and the engaged part 90. This configuration allows the inner plug 9 to bring the proximal side space inside the housing 8 and the distal side space inside the housing 8 into communication with each other so that the proximal side space S1 inside the barrel 6 and the distal side space S2 inside the barrel 6 communicate with each other. That is, the configuration is such that the inner plug 9 is opened relative to the inside of the housing 8 to achieve communication between the proximal side space S1 and the distal side space S2. That is, the partitioning device 7 is configured to have the inner plug 9 changing from the closed state (see FIG. 3) to the open state (see FIG. 4) by this pressing force. Specifically, when the pressing force is applied from the proximal side by the piston 3, at least one of the engaging part 81 and the engaged part 90 elastically deforms, the engaged part 90 crosses over or rides over the engaging part 81, and the inner plug 9 moves to the distal side to thereby release the engagement between the engaging part 81 and the engaged part 90, so that the inner plug 9 is opened relative to the inside of the housing 8 to achieve communication between the proximal side space S1 and the distal side space S2.

In the syringe 2, the barrel 6 and the attachment portion 83 of the housing 8 have the filter 80 sandwiched therebetween. Specifically, the filter 80 is held sandwiched in the axial direction between the proximal side end surface 600 of the distal end part 60 of the barrel 6 and the distal end surface 830 of the attachment portion 83. This configuration allows the filter 80 to be hardly detached from the attachment portion 83 for the filter 80 at the time of injecting the medical liquid even when the filter 80 is subjected to pressure.

Further, in the syringe 2, the proximal side space S1, the distal side space S2, and the outlet opening 64 are sequentially arranged in this order from the proximal side to the distal side. In the syringe 2 of this embodiment, the central axis of the proximal side space S1 and the central axis of the distal side space S2 both coincide with the central axis of the outlet opening 64. This configuration allows the medicine to favorably flow from the proximal side space S1 to the outlet opening 64 at the time of injecting the medicine.

The syringe 2 of this embodiment can be sterilized by radiation such as γ-rays. This sterilization can be performed by a gas such as ethylene oxide gas, or by autoclaving.

The piston 3 is a member operated when the medicine inside the barrel 6 is discharged. The piston 3 of this embodiment includes: a rod part 30 having a shaft shape; a gasket 31 attached to one end in a longitudinal direction of the rod part 30 and configured to be brought into close contact with the entire inner circumference of the cylindrical part 62 of the barrel 6; and an operating part 32 attached to the other end in the longitudinal direction of the rod part 30.

In the piston 3 of this embodiment, a distal end surface 33 is formed of a distal end surface of the gasket 31. Specifically, at the completion of injecting the medicine, the distal end surface 33 is brought into abutting contact with the end surface on the proximal side of the inner plug 9.

The piston 3 is operated by a physician, a nurse, or the like, but can be operated by a patient. In this case, the prefilled syringe 1 can be mounted to an autoinjector.

The injection needle 4 is a member for injecting the medicine inside the barrel 6 to a patient. The tip of the injection needle 4 is covered by the cap 5.

According to the syringe 2 configured as above, one of the engaging part 81 and the engaged part 90 in engagement with each other crosses over or rides over the other one with the pressing force by the piston 3 (in this embodiment, in the state where the engaging part 81 and the proximal side engaged part 901 engage with each other, the pressing force is applied to allow the proximal side engaged part 901 to cross over or ride over the engaging part 81) to thereby release the engagement at once. Thus, the partitioning device 7 for partitioning the space inside the barrel 6 is securely opened to achieve communication between the proximal side space S1 and the distal side space S2 for smooth discharge of the medical liquid.

In the syringe 2 of this embodiment, the configuration that one of the engaging part 81 and the engaged part 90 disposed on the distal side and the proximal side is located between portions of the other one (in this embodiment, the engaging part 81 is located between the proximal side engaged part 901 and the distal side engaged part 902) can restrict the inner plug 9 held in the closed state from moving in the axial direction to the distal side and the proximal side relative to the housing 8, and can restrict unintended movement of the inner plug 9 at the time of, for example, transportation.

In the syringe 2 of this embodiment, the filter 80 is disposed on the distal side end surface of the housing 8 and the partitioning device 7 is placed to partition the space inside the barrel 6 until the medicine is discharged can prevent the filter 80 from coming into contact with the medicine before the discharge if the medicine is contained in the proximal side space S1.

Further, in the syringe 2 of this embodiment, the configuration that the partitioning device 7 is disposed in the distal end part of the barrel 6 can prevent the filter 80 from coming into contact with the medicine contained in the proximal side space S1 until the medicine is discharged, and enables the filter 80 to filter the medicine after the partitioning device 7 placed for partitioning the space inside the barrel 6 is opened.

It is a matter of course that the syringe of the present invention is not limited to the aforementioned embodiment, but various modifications can be made without departing from the gist of the present invention. For example, a configuration of an embodiment can be added to a configuration of another embodiment, and part of a configuration of an embodiment can be replaced by a configuration of another embodiment. Further, part of a configuration of an embodiment can be deleted.

The configuration of the partitioning device 7 can be different from the aforementioned configuration. For example, the inner plug 9 can include the engaged part 90, and can have a different configuration from the aforementioned configuration.

Specifically, as shown in FIG. 7 to FIG. 12, the inner plug 9 can include no annular portion 96. That is, it is conceivable that the inner plug 9 include the engaged part 90, the lid portion 92 covering the proximal side space S1, the leg portions 94 (specifically four leg portions 94) extending from the lid portions 92, the plurality of projecting portions 95 (specifically, four projecting portions 95) projecting from the respective leg portions 94 toward the housing 8 (i.e., radially outward).

The inner plug 9 can include the connecting portion that connects the lid portion 92 (specifically, the lid leg 922 of the lid portion 92) and the leg portions 94 to each other. In this case, when the inner plug 9 is pressed by the piston 3, the connecting portion can restrict the leg portions 94 from being bent in the radial direction in the state where the step engaging parts 93 (projecting portions 95) are in engagement with the stepped surface 810.

Further, the inner plug 9 can include, instead of the annular portion 96, a plug extension portion extending in the circumferential direction from the respective ends on the housing 8 side (i.e., radially outside ends) of the projecting portions 95. The configuration can be, for example, such that the plug extension portion extends from each of the projecting portions 95 and includes a plurality of the plug extension portions. The configuration can be such that the plurality of plug extension portions are disposed at intervals from each other in the circumferential direction.

The configuration can also be such that the inner plug 9 includes neither the leg portions 94 nor the projecting portions 95, and is composed of the engaged part 90 and the lid portion 92.

The aforementioned embodiment has been described by taking, for example, the case where, when the pressing force is applied from the proximal side by the piston 3, at least one of the engaging part 81 and the engaged part 90 elastically deforms, the engaged part 90 crosses over or rides over the engaging part 81, and the inner plug 9 moves to the distal side to release the engagement between the engaging part 81 and the engaged part 90. However, the configuration can be such that, when this pressing force is applied, at least one of the engaging part 81 and the engaged part 90 elastically deforms, the engaging part 81 crosses over or rides over the engaged part 90, and the housing 8 moves to the distal side to release the engagement between the engaging part 81 and the engaged part 90.

Even with such a configuration, one of the engaging part 81 and the engaged part 90 in engagement with each other crosses over or rides over the other one with the pressing force by the piston 3 to thereby release the engagement at once. Thus, the partitioning device 7 for partitioning the space inside the barrel 6 is securely opened to achieve communication between the proximal side space S1 and the distal side space S2 for smooth discharge of the medical liquid.

The aforementioned embodiment has been described by, taking, for example, the case where the partitioning device 7 includes one engaging part 81 and the plurality of (specifically, two) engaged parts 90, but the configuration can be such that the partitioning device 7 includes a plurality of engaging parts 81 and one engaged part 90. Specifically, the configuration can be such that the engaging parts 81 are disposed on the distal side and the proximal side of the engaged part 90. In such a case, a recess can be formed between the engaging parts 81 disposed on the distal side and the proximal side in the housing 8. The engaged part 90 of the inner plug 9 is fitted to this recess from the radially inside. In this fitted state, one of the engaging parts 81 disposed on the proximal side engages with the engaged part 90 from the distal side to restrict the inner plug 9 from moving to the proximal side relative to the housing 8. Further, in the fitted state, the other one of the engaging parts 81 disposed on the distal side engages with the engaged part 90 from the distal side to restrict the inner plug 9 from moving to the distal side relative to the housing 8. The configuration can be such that the partitioning device 7 includes one engaging part 81 and one engaged part 90.

Figures 13A, 13B, 13C, 13D:
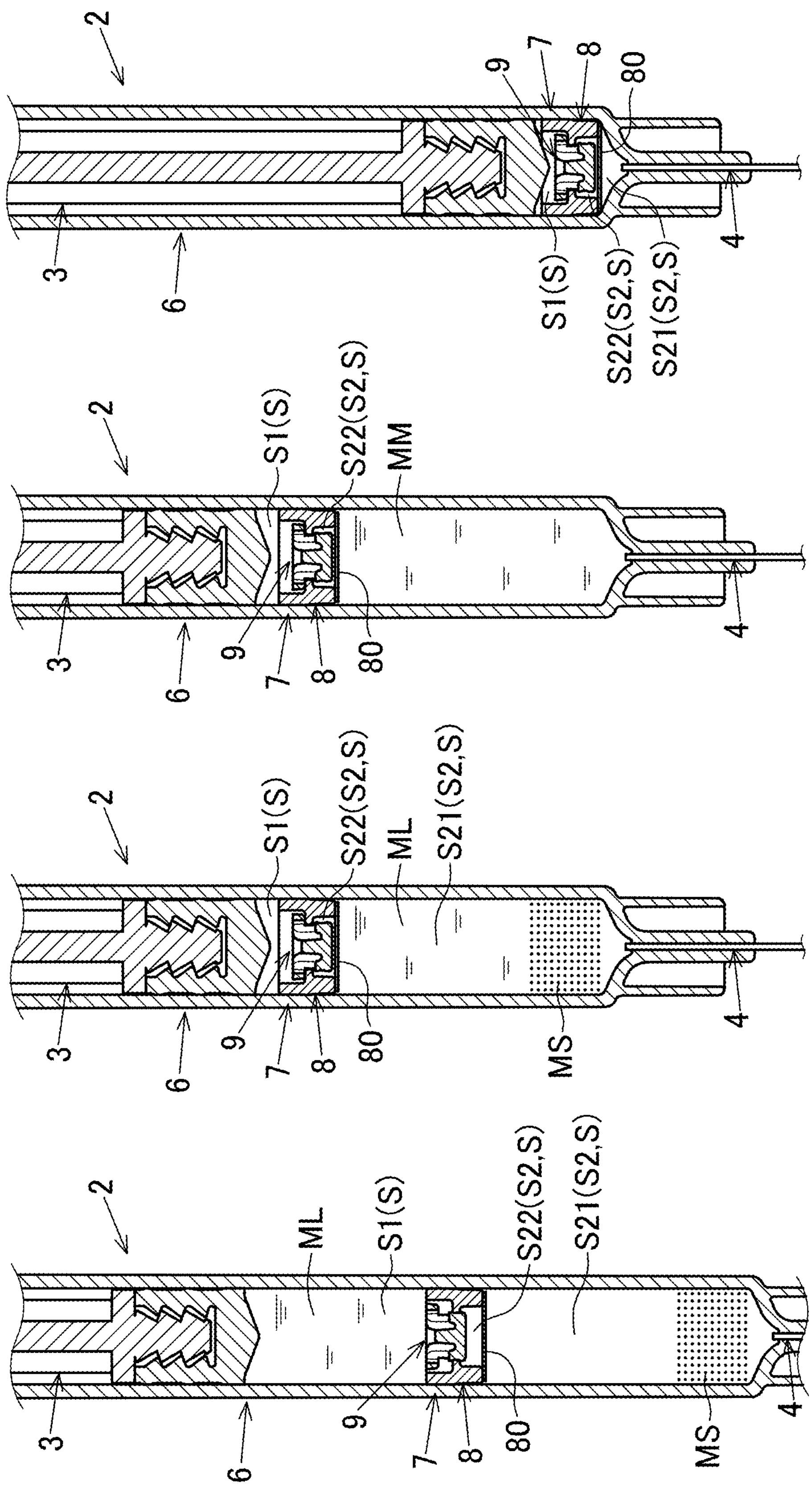
FIG. 13A is a schematic cross-sectional view of a prefilled syringe according to a modified example when in use, and shows a closed state of an inner plug.
FIG. 13B is a schematic cross-sectional view of the prefilled syringe according to the modified example when in use, and shows a state immediately after the inner plug is opened.
FIG. 13C is a schematic cross-sectional view of the prefilled syringe according to the modified example when in use, and shows an open state of the inner plug.
FIG. 13D is a schematic cross-sectional view of the prefilled syringe according to the modified example when in use, and shows a state after a medicine is injected.

The aforementioned embodiment has been described by taking, for example, the case where the partitioning device 7 is disposed at the distal end part 60 of the barrel 6, but the configuration can be such that the barrel 6 is disposed at an intermediate position in the axial direction of the barrel 6. For example, the configuration can be such that the partitioning device 7 is disposed at an intermediate position in the axial direction of the barrel 6 to partition the proximal side space S1 and the distal side space S2, in which state a liquid medicine ML is contained in the proximal side space S1 and a solid medicine MS is contained in the distal side space S2 (specifically, the first distal side space S21) (see FIG. 13A). When, in this state, the pressing force is applied from the proximal side by the piston 3 and the inner plug 9 is opened relative to the inside of the housing 8 to achieve communication between the proximal side space S1 and the distal side space S2 as shown in FIG. 13B, the liquid medicine ML flows from the proximal side space S1 into the distal side space S2 to obtain a mixture medicine MM in which the solid medicine MS and the liquid medicine ML are mixed together, as shown in FIG. 13C. Further, the pressing force applied from the proximal side by the piston 3 can inject the mixture medicine MM as shown in FIG. 13D.

As described above, in this embodiment, the partitioning device 7 is disposed at an intermediate position in the axial direction of the barrel 6 to partition the space inside the barrel 6 into the proximal side space S1 and the distal side space S2. The partitioning device 7 is configured to be opened when the pressure by the piston 3 from the proximal side space S1 side reaches a certain pressure, and to move to the distal end part 60 of the barrel 6 while being held opened in association with the pushing operation of the piston 3 to the distal side of the barrel 6.

Since the partitioning device 7 for partitioning the space into the proximal side space S1 and the distal side space 7 includes the filter 80, unwanted solid matters are captured by the filter 80 when the partitioning device 7 is opened to allow the liquid medical ML to flow from the proximal side space S2 into the distal side space S2.

Figure 14A:
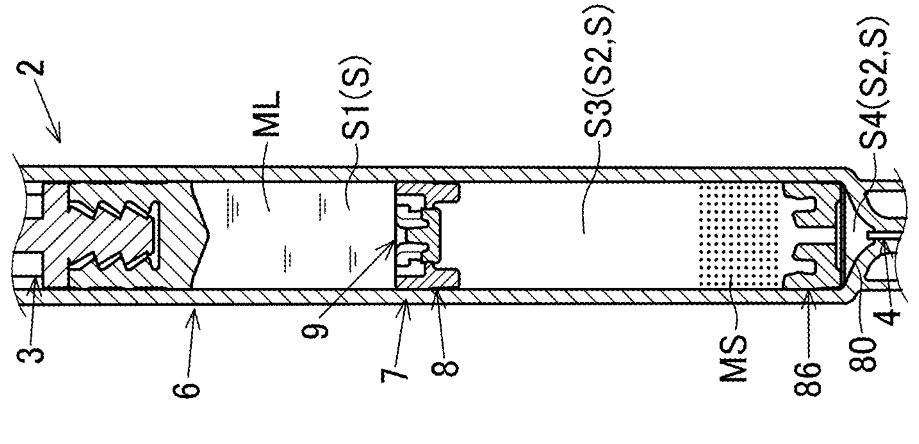
FIG. 14A is a schematic cross-sectional view of a prefilled syringe according to a modified example when in use, and shows a closed state of an inner plug.

The configuration can be such that the partitioning device 7 includes no filter 80. For example, as shown in FIG. 14A, it is conceivable that the partitioning device 7 include only the housing 8 and the inner plug 9 and be disposed at an intermediate position of the barrel 6, and that a filter member 86 including the filter 80 be disposed on the distal side of the partitioning device 7 so as to be away from the partitioning device 7.

Even in this case, it is still conceivable that the space S inside the barrel 6 be partitioned by the partitioning device 7 into the proximal side space S1 as a space on the proximal side of the housing 8 and the inner plug 9 and the distal side space S2 as a space on the distal side of the housing 8 and the inner plug 9. In this embodiment, the distal side space S2 includes a third distal side space S3 as a space between the filter member 86 and the housing 8/the inner plug 9, and a fourth distal side space S4 as a space on the distal side of the filter member 86. In this configuration, it is conceivable that the proximal side space S1 contain the liquid medicine ML, the third distal side space S3 contain the liquid medicine ML or the solid medicine MS, and the fourth distal side space S4 contain the solid medicine MS or be empty. In this embodiment, the proximal side space S1 contains the liquid medicine ML, the third distal side space S3 contains the solid medicine MS, and the fourth distal side space S4 is empty.

In this partitioning device 7, the housing 8 includes no filter 80 but the filter member 86 includes the filter 80. The housing 8 and the filter member 86 both have a substantially cylindrical shape. In this embodiment, the inner circumferential surface of the filter member 86 has a smaller diameter than that of the inner circumferential surface of the housing 8, but the inner circumferential surface of the filter member 86 can be formed to have substantially the same diameter as that of the inner circumferential surface of the housing 8.

Figure 14B:
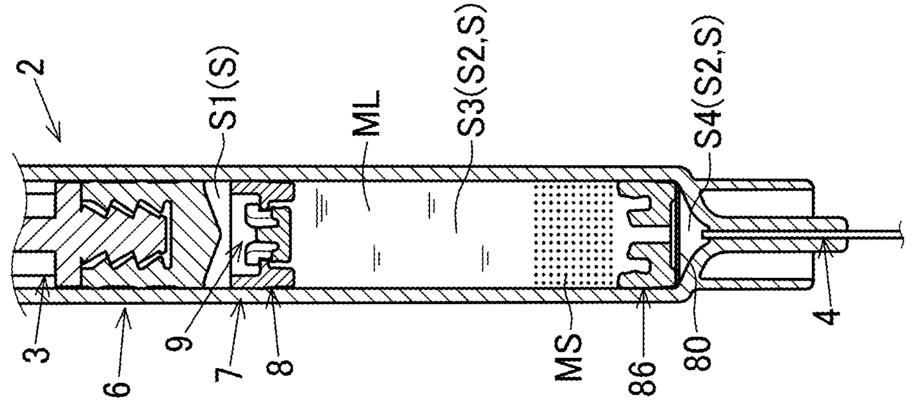
FIG. 14B is a schematic cross-sectional view of the prefilled syringe according to the modified example when in use, and shows a state immediately after the inner plug is opened.
Figure 14C:
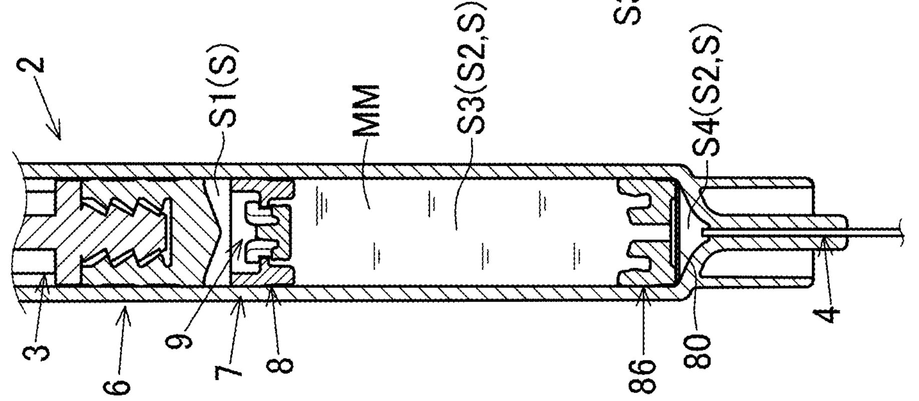
FIG. 14C is a schematic cross-sectional view of the prefilled syringe according to the modified example when in use, and shows an open state of the inner plug.
Figure 14D:
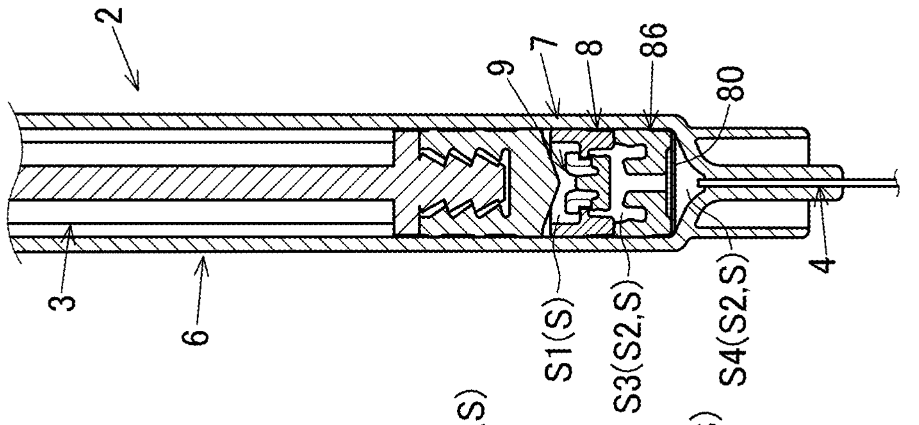
FIG. 14D is a schematic cross-sectional view of the prefilled syringe according to the modified example when in use, and shows a state after a medicine is injected.
Figure 15:
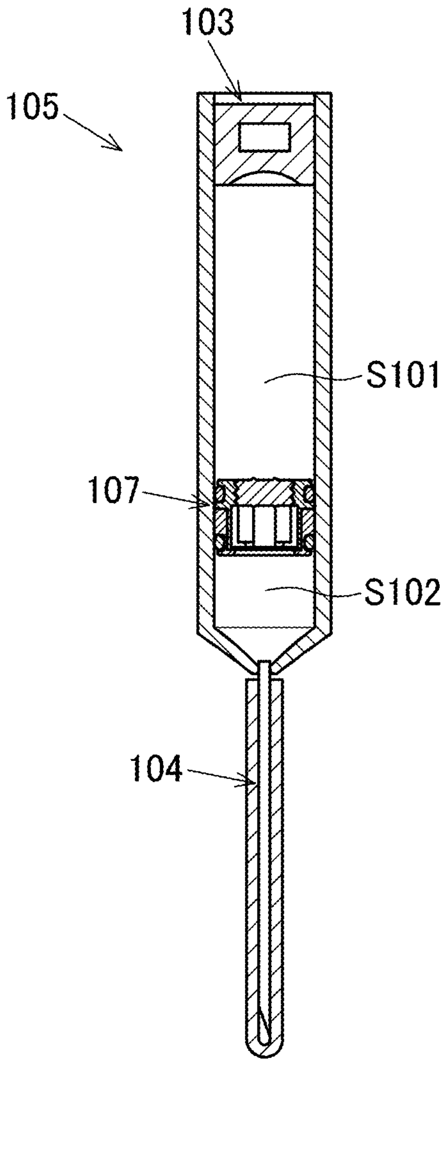
FIG. 15 is a cross-sectional view for explaining a conventional syringe.
Figure 16:
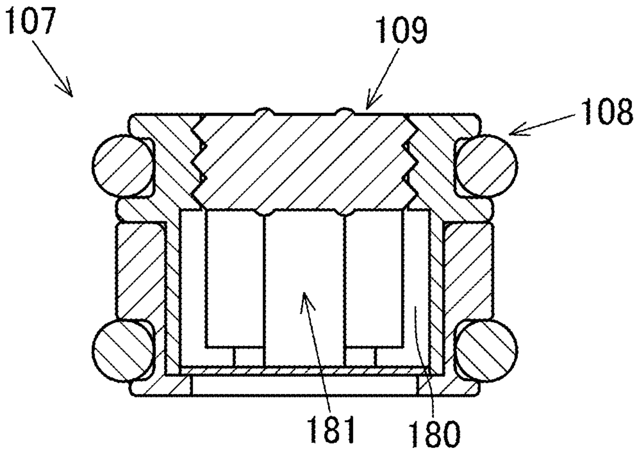
FIG. 16 is an enlarged cross-sectional view of an essential part of the conventional syringe.
Figure 17:
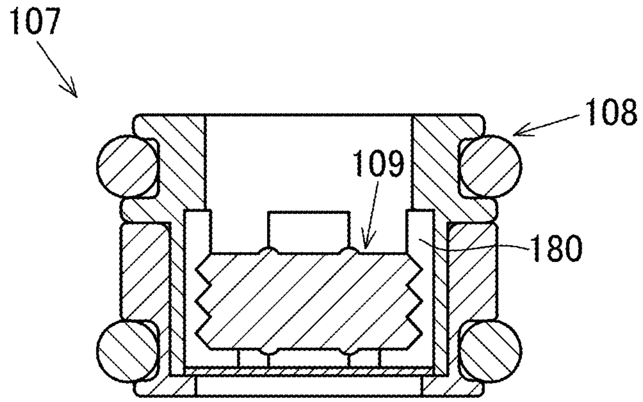
FIG. 17 is an enlarged cross-sectional view of an essential part of the conventional syringe.

In this configuration, in the state where the partitioning device 7 is placed to partition the space into the proximal side space S1 and the third distal side space S3, the liquid medical ML contained in the proximal side space S1 and the solid medicine MS contained in the third distal side space S3 are separated by the partitioning device 7. In this state, when the pressing force is applied from the proximal side by the piston 3 and the inner plug 9 is opened relative to the inside of the housing 8 to achieve communication between the proximal side space S1 and the third distal side space S3 as shown in FIG. 14B, the liquid medicine ML flows from the proximal side space S1 into the third distal side space S3 to obtain the mixture medicine MM in which the solid medicine MS and the liquid medicine ML are mixed together, as shown in FIG. 14C. Further, the pressing force applied from the proximal side by the piston 3 can inject the mixture medicine MM as shown in FIG. 14D.

As described above, the partitioning device 7 including the housing 8 and the inner plug 9 is disposed at an intermediate position in the axial direction of the barrel 6 to partition the space S inside the barrel 6 into the proximal side space S1 and the distal side space S2, and is configured to be opened when the pressure by the piston 3 from the proximal side space S1 side reaches a certain pressure, and to move to the distal end part 60 of the barrel 6 while being held opened in association with the pushing operation of the piston 3 to the distal side of the barrel 6. This configuration includes the filter member 86 disposed on the distal side of the housing 8 and having a flow hole communicating from the proximal side to the distal side, and the filter 80 attached to the filter member 86 and filtering a liquid flowing through the flow hole. Thus, unwanted solid matters are captured by the filter 80 when the inner plug 9 is opened relative to the housing 8 to allow the liquid medicine ML to flow from the proximal side space S1 into the distal side space S2 and be mixed with the solid medicine MS for discharge through the distal end part 60 of the barrel 6. Since the filter member 86 is disposed not to move to the distal side in the distal end part 60 of the barrel 6, the pushing resistance of the piston 3 can be equalized when the housing 8 moves to the distal side.

Further, for example, it is conceivable that the partitioning device 7 include two sets each composed of the housing 8 and the inner plug 9, and one of the two sets be disposed on the proximal side while the other set be disposed on the distal side so as to be away from the one set. In this case, it is conceivable that a space on the proximal side of those housing 8 and inner plug 9 located on the proximal side contain the liquid medicine ML, a space between those housing 8 and inner plug 9 located on the proximal side and those housing 8 and inner plug 9 located on the distal side contain the liquid medicine ML or the solid medicine MS, and a space on the distal side of those housing 8 and inner plug 9 located on the distal side contain the solid medicine MS or be empty.

In the case where the plurality of engaging parts 81 are provided at intervals from each other across the entire circumference in the circumferential direction, the configuration can be such that the plurality of engaging parts 81 are disposed to be opposed to each other with the cylindrical axis therebetween. The configuration can also be such that the plurality of engaging parts 81 are disposed at equal intervals from each other in the circumferential direction. In the case where the plurality of engaged parts 90 are similarly disposed at intervals from each other across the entire circumference in the circumferential direction, the configuration can be such that the plurality of engaged parts 90 are disposed to be opposed to each other with the cylindrical axis therebetween, or disposed at equal intervals in the circumferential direction. Such a configuration enables stable engagement between the engaging parts 81 and the engaged parts 90, and thus the inner plug 9 can hardly come off the housing 8 during the transportation of the syringe 2.

According to the present invention, provided can be a syringe in which a partitioning device for partitioning a space inside a barrel can be opened when in use for smooth discharge of a medical liquid.

A syringe of the present invention is a syringe for injecting a medicine, the syringe including: a barrel having a cylindrical shape with a distal end part and a proximal end part and having an outlet opening in the distal end part for discharging the medicine contained inside the barrel to an outside; and a partitioning device for partitioning a space inside the barrel into a proximal side space and a distal side space, the partitioning device including: a cylindrical housing disposed to come into liquid-tight contact with an inner surface of the barrel; and an inner plug disposed to allow a proximal side space inside the housing and a distal side space inside the housing to be opened and closed so that the proximal side space inside the barrel and the distal side space inside the barrel are brought into or out of communication with each other through an inside of the housing, the housing including an engaging part configured to engage with the inner plug when the proximal side space inside the housing and the distal side space inside the housing are not in communication with each other, the inner plug including an engaged part configured to engage with the engaging part from a proximal side when the proximal side space inside the housing and the distal side space inside the housing are not in communication with each other, and the partitioning device being configured so that, when a pressing force is applied from the proximal side by a piston inserted from the proximal side into the barrel, one of the engaging part and the engaged part is displaced relative to an other one of the engaging part and the engaged part to cross over or ride over the other one and release engagement between the engaging part and the engaged part, thereby allowing the inner plug to have the proximal side space inside the housing and the distal side space inside the housing communicating with each other to achieve communication between the proximal side space inside the barrel and the distal side space inside the barrel.

According to such a configuration, one of the engaging part and the engaged part in engagement with each other crosses over or rides over the other one with the pressing force by the piston to thereby release the engagement at once; thus, the partitioning device for partitioning the space inside the barrel can be securely opened to achieve communication between the proximal side space and the distal side space for smooth discharge of the medical liquid.

The syringe can be configured such that the engaging part includes a proximal side engaging part and a distal side engaging part disposed respectively on a proximal side and a distal side of the engaged part, or the engaged part includes a proximal side engaged part and a distal side engaged part disposed respectively on a proximal side and a distal side of the engaging part.

According to such a configuration, one of the engaging part and the engaged part disposed on the distal side and the proximal side is located between portions of the other one; thus, the inner plug in the closed state can be restricted from moving in the axial direction to the distal side and the proximal side relative to the housing.

The syringe can be configured to further include a filter disposed on a distal side end surface of the housing inside the barrel.

According to such a configuration, the partitioning device is placed to partition the space inside the barrel until the medicine is discharged; thus, the filter can be prevented from coming into contact with the medicine before the discharge if the medicine is contained in the proximal side space.

The syringe can be configured such that the partitioning device is disposed in the distal end part of the barrel.

According to such a configuration, the filter can be prevented from coming into contact with the medicine contained in the proximal side space until the medicine is discharged, and can filter the medicine after the partitioning device placed for partitioning the space inside the barrel is opened.

REFERENCE SIGNS LIST

1: Prefilled syringe
2: Syringe
3: Piston
4: Injection needle
5: Cap
6: Barrel
7: Partitioning device
8: Housing
9: Inner plug
30: Rod part
31: Gasket
32: Operating part
33: Distal end surface
60: Distal end part
61: Proximal end part
62: Cylindrical part
63: Flange part
64: Outlet opening
80: Filter
81: Engaging part
82 Inner circumferential surface
83: Attachment portion
84: Body portion
85: Extending portion
86: Filter member
90: Engaged part
91: Restricting device
92: Lid portion
93: Step engaging part
94: Leg portion
95: Projecting portion
96: Annular portion
97: Lid recess
98: Abutting surface
103: Plunger
104: Needle
105: Chamber
107: Sealing mechanism
108: Outer sealing member
109: Sealing plug
180: Groove
181: Flow channel
600: Proximal side end surface
800: Outer circumferential surface
801: Proximal outer circumferential surface part
802: Distal outer circumferential surface part
810: Stepped surface
821: Proximal inner circumferential surface part
822: Distal inner circumferential surface part
830: Distal end surface
901: Proximal side engaged part
902: Distal side engaged part
920: Outer circumferential part
921: Inner circumferential part
922: Lid leg
S: Space
S1: Proximal side space
S2: Distal side space
S21: First distal side space
S22: Second distal side space
S3: Third distal side space
S4: Fourth distal side space
S101: Wet portion
S102: Dry portion
C8: Liquid flow channel
C9: Plug channel
C91: Axial channel
C92: Communicating channel
ML: Liquid medicine
MS: Solid medicine
MM: Mixture medicine

The invention claimed is:

1. A syringe for injecting a medicine, the syringe comprising:

a barrel having a cylindrical shape with a distal end part and a proximal end part and having an outlet opening in the distal end part for discharging the medicine contained inside the barrel to an outside; and a partitioning device for partitioning a space inside the barrel into a proximal side space and a distal side space, the partitioning device comprising:

a cylindrical housing disposed to come into liquid-tight contact with an inner surface of the barrel; and an inner plug disposed to allow a proximal side space inside the housing and a distal side space inside the housing to be opened and closed so that the proximal side space inside the barrel and the distal side space inside the barrel are brought into or out of communication with each other through an inside of the housing, the housing comprising an engaging part that is configured to engage with the inner plug when the proximal side space inside the housing and the distal side space inside the housing are not in communication with each other, the inner plug comprising an engaged part that is configured to engage with the engaging part from a proximal side when the proximal side space inside the housing and the distal side space inside the housing are not in communication with each other, and the partitioning device being configured so that, when a pressing force is applied from the proximal side by a piston inserted from the proximal side into the barrel, one of the engaging part and the engaged part is displaced relative to an other one of the engaging part and the engaged part to cross over or ride over the other one and release engagement between the engaging part and the engaged part, thereby allowing the inner plug to have the proximal side space inside the housing and the distal side space inside the housing communicating with each other to achieve communication between the proximal side space inside the barrel and the distal side space inside the barrel, wherein the engaging part comprises a proximal side engaging part and a distal side engaging part disposed respectively on a proximal side and a distal side of the engaged part, or the engaged part comprises a proximal side engaged part and a distal side engaged part disposed respectively on a proximal side and a distal side of the engaging part, and the syringe further comprises a filter disposed on a distal side end surface of the housing inside the barrel.

2. The syringe according to claim 1, wherein the partitioning device is disposed in the distal end part of the barrel.

* * * * *